(12) United States Patent
Wegener (10) Patent No.: US 12,279,609 B2
(45) Date of Patent: *Apr. 22, 2025

(54) SYSTEM FOR WASHING RED BLOOD CELLS TO REDUCE HEMOLYSIS

(71) Applicant: Fenwal, Inc., Lake Zurich, IL (US)

(72) Inventor: Christopher J. Wegener, Libertyville, IL (US)

(73) Assignee: Fenwal, Inc., Lake Zurich, IL (US)

( * ) Notice: Subject to any disclaimer, the term of this patent is extended or adjusted under 35 U.S.C. 154(b) by 277 days.

This patent is subject to a terminal disclaimer.

(21) Appl. No.: 17/589,454

(22) Filed: Jan. 31, 2022

(65) Prior Publication Data

US 2022/0151222 A1 May 19, 2022

Related U.S. Application Data

(63) Continuation of application No. 15/579,102, filed as application No. PCT/US2016/032301 on May 13, 2016, now Pat. No. 11,252,955.

(60) Provisional application No. 62/169,029, filed on Jun. 1, 2015.

(51) Int. Cl.
| | |
|---|---|
| *A01N 1/02* | (2006.01) |
| *A61K 35/14* | (2015.01) |
| *A61M 1/02* | (2006.01) |
| *A61M 1/36* | (2006.01) |
| *C12N 5/078* | (2010.01) |

(52) U.S. Cl.
CPC ............ *A01N 1/0226* (2013.01); *A61K 35/14* (2013.01); *A61M 1/0281* (2013.01); *A61M 1/3609* (2014.02); *A61M 1/3692* (2014.02); *A61M 1/3693* (2013.01); *C12N 5/0634* (2013.01)

(58) Field of Classification Search
CPC .............. A61M 1/0281; A61M 1/3609; A61M 1/3692; A61M 1/3693
See application file for complete search history.

(56) References Cited

U.S. PATENT DOCUMENTS

| | | | |
|---|---|---|---|
| 5,250,303 | A | 10/1993 | Meryman et al. |
| 11,252,955 | B2 * | 2/2022 | Wegener ............ A61M 1/3692 |
| 2007/0020607 | A1 | 1/2007 | Meryman et al. |
| 2012/0225419 | A1 | 9/2012 | Min et al. |

(Continued)

OTHER PUBLICATIONS

International Preliminary Report on Patentability for International Application No. PCT/US2016/032301 issued Dec. 5, 2017.

(Continued)

*Primary Examiner* — Leslie R Deak
(74) *Attorney, Agent, or Firm* — Cook Alex Ltd.

(57) ABSTRACT

A system for washing red blood cells, comprising a separator configured to separate a quantity of blood into concentrated red blood cells having a hematocrit of at least 60% and a volume of 150-250 mL, and a supernatant component. The system comprises a flow controller configured to remove the supernatant component to provide an initial red blood cell concentrate; combine 50-500 mL of an additive solution with the red blood cell concentrate to provide an intermediate red blood cell product intended for storage for 42 days or less; and wash the intermediate red blood cell product with a washing solution.

20 Claims, 8 Drawing Sheets

(56) References Cited

U.S. PATENT DOCUMENTS

2013/0220925 A1 8/2013 Min et al.
2016/0177262 A1 6/2016 Wegener et al.

OTHER PUBLICATIONS

Zehnder et al., Erythrocyte storage in hypertonic (SAGM) or isotonic (PAGGSM) conservation medium: influence on cell properties, Vox Sanguinis, vol. 95, No. 4 (Nov. 2008) pp. 280-287. (Year: 2008).

* cited by examiner

| Diluent | Osmolarity (mOsm/L) | % Hemolysis |
|---|---|---|
| AS-1 Stored RCC | 338-369 | ~0.28% |
| 0.7% Saline | ~202-214 | ~0.81% |
| 0.9% Saline | 265-287 | ~0.40% |
| 1.1% Saline | 330-342 | ~0.27% |
| 1.3% Saline | 392-409 | ~0.26% |
| 1.5% Saline | 456-473 | ~0.25% |
| AS-1 | 445-466 | ~0.26% |
| PBS | 283-294 | ~0.33% |
| CPD | 464-479 | ~0.26% |
| ACD-A | 311-323 | ~0.36% |

SYSTEM FOR WASHING RED BLOOD CELLS TO REDUCE HEMOLYSIS

CROSS-REFERENCE TO RELATED APPLICATIONS

This application is a continuation of U.S. patent application Ser. No. 15/579,102, submitted under 35 U.S.C. § 371 on Dec. 1, 2017, and is the U.S. National Stage of International Application No. PCT/US2016/032301, filed on May 13, 2016, which claims the benefit of U.S. Provisional Patent App. No. 62/169,029, filed Jun. 1, 2015, all of which are expressly incorporated herein by reference in their entireties.

FIELD OF THE DISCLOSURE

The present disclosure is directed to a system for washing red blood cells, more particularly, to a system for washing red blood cells with a wash media having a specific osmolarity value, to reduce hemolysis of cells.

BACKGROUND

The administration of blood and/or blood components is common in the treatment of patients suffering from disease or blood loss. Rather than infuse whole blood, individual components may be administered to the patient in need. For example, administration (infusion) of platelets may be prescribed for cancer patients whose ability to make platelets has been compromised by chemotherapy. Red blood cells may be administered to patients who have suffered a loss of blood, anemia, or other disorders. Infusion of plasma may also be prescribed for therapeutic reasons, and the harvesting and processing of white blood cells has received widespread interest within the medical community. Thus, it is often desirable to separate and collect a blood component, (e.g., red blood cells, platelets, plasma, white blood cells) from whole blood and then treat the patient with the specific blood component. The remaining components may be returned to the donor or collected for other uses.

Several factors may be considered in the separation, collection, and storage of blood components for subsequent transfusion. For example, the presence of white blood cells (e.g., leukocytes) in a blood component collected for administration may be undesirable as such leukocytes can trigger an adverse response in the recipient-patient. As a result, blood components are often "leukoreduced" prior to transfusion. Also, the presence of certain antibodies in plasma has been correlated with the occurrence of TRALI (transfusion-related acute lung injury) in some patients receiving blood components such as red blood cells. Consequently, while plasma may be present to some degree in transfusible red blood cells and platelets, it can be desirable to reduce the amount of plasma in the red blood cell or platelet preparation. Also, extracellular components (e.g., K+, IgA, lactate, free hemoglobin, etc.) may be released by the lysis of cells during the collection, storage, and washing process and may be desirable to wash out.

Red blood cells are often stored for long periods of time prior to transfusion. In this case, it is desirable for the environment in which the cells are stored to be carefully controlled to optimize and/or maintain cell properties required for effective transfusion. For example, it is usually desirable to limit hemolysis during storage of the RBCs or during washing of the RBCs prior to transfusion. Also, stored red blood cell concentrates (RCCs) are commonly washed prior to transfusion to remove undesirable extracellular components from the cells while maintaining the integrity and functionality of the cells, so that the probability of immunological reaction in patients is decreased. It is an aim of the wash process to maximize removal of undesirable extracellular components while minimizing cell hemolysis and resulting release of free hemoglobin into the surrounding plasma.

SUMMARY

According to an exemplary embodiment, the present disclosure is directed to a system for washing red blood cells, comprising a separator configured to separate a quantity of blood into concentrated red blood cells having a hematocrit of at least 60°/c; and a volume of 150-250 mL, and a supernatant component. The system comprises a flow controller in communication with the separator. The flow controller is configured to remove the supernatant component to provide an initial red blood cell concentrate. The flow controller is configured to combine 50-500 mL of an additive solution with the red blood cell concentrate to provide an intermediate red blood cell product that is intended for storage for a period of time of 42 days or less. The intermediate red blood cell product at the end of storage has an osmolarity value between 202-479 mOsm/L. The flow controller is configured to wash the intermediate red blood cell product comprising the osmolarity value between 202-479 mOsm/L with a washing solution having an osmolarity value higher than that of the intermediate red blood cell product comprising the osmolarity value between 202-479 mOsm/L.

According to an exemplary embodiment, the present disclosure is directed to a system for washing red blood cells, comprising a separator configured to separate a quantity of blood into concentrated red blood cells and a supernatant component. The system also comprises a flow controller in communication with the separator. The flow controller is configured to remove said supernatant component to provide an initial red blood cell concentrate, combine an additive solution with said red blood cell concentrate to provide an intermediate red blood cell product that is intended for storage for a period of time, and wash the intermediate red blood cell product that has been stored for a period of time with a washing solution having an osmolarity value higher than that of the intermediate red blood cell product.

According to an exemplary embodiment, the present disclosure is directed to a system for processing blood cells comprising a flow controller configured to add a selected volume of additive solution to a quantity of blood. The system also comprises a separator in communication with the flow controller configured to separate the quantity of blood into concentrated red blood cells and a supernatant component, wherein the supernatant component comprises at least plasma and additive solution, and wherein the concentrated red blood cell component comprises red blood cells and a volume of remaining supernatant. The flow controller is configured to wash the concentrated red blood cell component with a wash media comprising an osmolarity value higher than the osmolarity value of the concentrated red blood cell component, and remove substantially all of the wash media and remaining supernatant to provide a treated red blood cell concentrate. A percentage of red cells that have undergone hemolysis during washing and removal of wash media is less than 0.3% of the red cells from the concentrated red blood cell component.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may decrease hemolysis of blood cells during the washing process and decrease free hemoglobin levels in the blood product.

The systems and methods of the present disclosure may be used to establish or control the conditions under which red blood cell products may be stored and washed before transfusion. Thus, the methods may be used to introduce additive solutions, washing solutions, or reagents that may improve the storage and washing properties of the red blood cells, thereby providing a transfusible red blood cell product.

In one embodiment, a method for providing readily transfusible, red cells disclosed herein (and depicted in FIG. 1) includes providing a quantity of blood at step 201a, typically in a container. As used herein, the term "blood" is meant to include unfractionated and typically anticoagulated whole blood as well as a red blood cell concentrate that has been previously derived (i.e., separated) from whole blood. Thus, for example, the blood may be a packed or concentrated red blood cells (i.e., red blood cell concentrate) having a hematocrit of approximately 60%.

Figure 1:
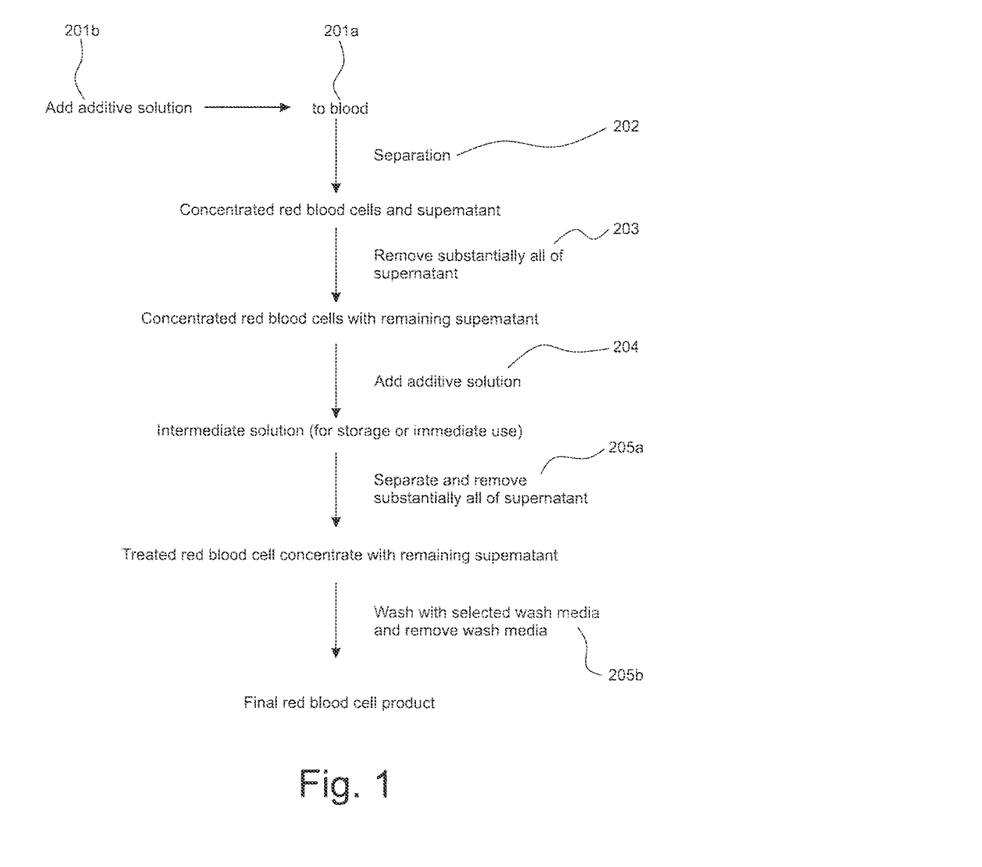
FIG. 1 is a flow diagram generally showing a method for providing readily transfusible red cells, according to an exemplary embodiment.

Preferably, however, the "blood" is provided as whole blood in a container which can be a blood processing, collection, or storage container of the type conventionally used in so-called "manual" or "whole blood" processing, or containers such as those used in automated apheresis. With regard to automated apheresis, the container in which the separation of blood or the processing of blood components may occur may also refer to the chamber of the separation device, such as a centrifuge or spinning membrane. Non-limiting examples of these are the separation chambers used in the Alyx@) separator, Amicus® separator and Autopheresis-C@ separator, all made and sold by Fenwal, Inc. of Lake Zurich, Ill. Regardless of whether the "blood" is provided as unfractionated whole blood or an already separated-from whole blood red blood cell concentrate, the blood is separated (for the first time or further separated, depending on the composition of the starting "blood") into red blood cell concentrate and plasma, including any residual anticoagulant from the initial draw.

Where the source of blood is whole blood at step 201, a typical volume of whole blood is approximately 400-500 mL. The blood may be spun at step 202 to preferably result in a red blood cell concentrate having a hematocrit of preferably at least 90%. Plasma and residual anticoagulant form a supernatant layer, while the volume of the red blood cell concentrate separated from the supernatant may be approximately 150-250 mL. Once the desired volume of the packed red blood cells or red blood cell concentrate has been obtained, physical separation and removal of substantially all of the supernatant plasma layer (with anticoagulant) from the red blood cells may take place at step 203. Not all of the supernatant, however, may have been removed and therefore the initial red blood cell concentrate may typically include about 10-30 mL of remaining supernatant.

With substantially all of the plasma (and anticoagulant) of the supernatant removed, a selected quantity or volume of additive solution may be added at step 204 to the initial red blood cell concentrate remaining in the initial container in which the whole blood (or other "blood") was provided, or in a separate container. A non-limiting example of an additive solution is Adsol®, made and sold by Fenwal, Inc. of Lake Zurich, Ill. The volume of additive solution added to the initial red blood cell concentrate may be anywhere between approximately 50-500 mL, with between about 100-300 mL being preferred. The initial red blood cell concentrate that has been combined with the selected volume of additive solution is referred to herein as the "intermediate" blood cell product. The intermediate blood cell product preferably includes between approximately 150-250 mL, and more preferably approximately 200 mL of red blood cells, approximately 10-30 mL of the remaining supernatant and the added volume of additive solution as described above.

The intermediate blood cell product may then be washed immediately (steps 205a and 205b) and used and/or stored until use or transfusion. If stored, the period of storage may vary but preferably not over 42 days. Whether the wash process takes place immediately or after storage, the wash solution may impact the health of the blood cell product. In manual and automated wash processes, it is not uncommon for extracellular components (e.g., K+, IgA, lactate, etc.) to be successfully washed out, while free hemoglobin levels in the washed product remain more elevated than desired. Typical wash protocols involve steps that include washing an intermediate blood cell product with one or more washing fluids. The nature of the washing fluid used may influence the efficiency with which extracellular components are washed out while preventing further lysis of red cells and thereby minimizing free hemoglobin levels.

A study was conducted to evaluate washing fluid properties, and it was found that washing fluids with an osmolarity greater than that of the intermediate blood cell product produced reduced levels of cell lysis and free hemoglobin while successfully washing away the extracellular components.

Figure 2:
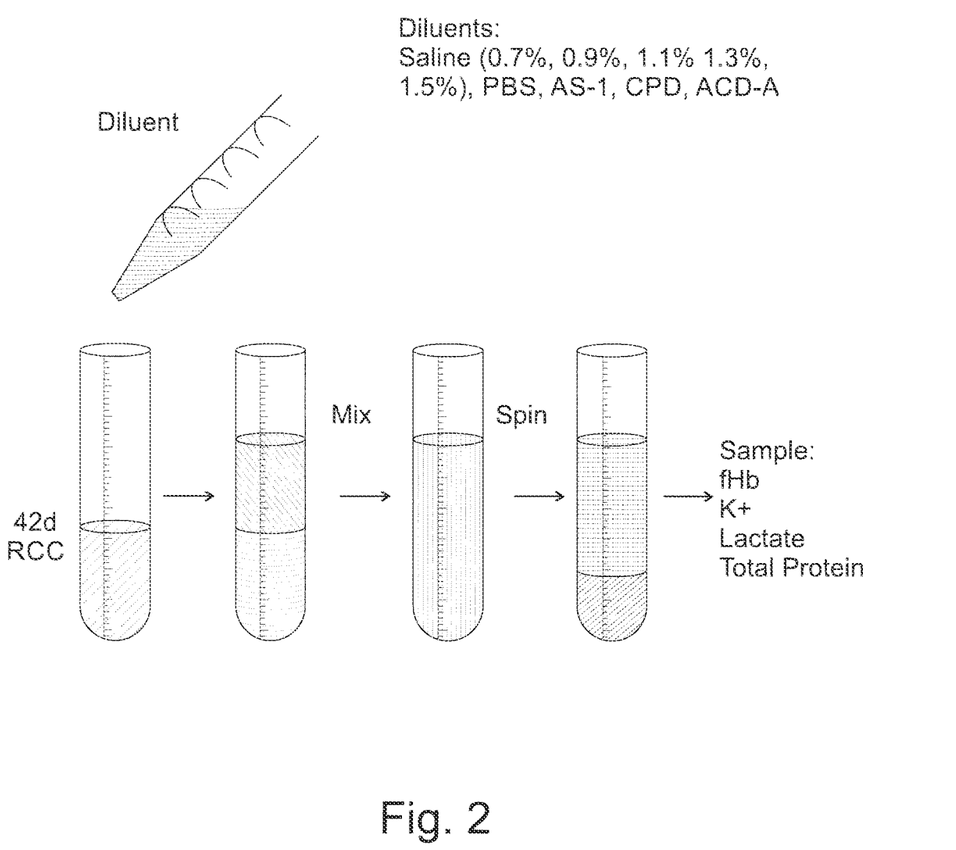
FIG. 2 is a flow diagram generally showing the methods of a study conducted to evaluate washing fluid properties, according to an exemplary embodiment.

In the study, as depicted in FIG. 2, whole blood units (n=13) were collected into CPD anticoagulant and each separated via traditional hard-spin centrifugation into plasma and a red cell concentrate (RCC). 110 mL of Adsol (containing glucose, mannitol, adenine, sodium chloride, and water) was added to each red cell concentrate to produce an intermediate RCC product, followed by leukoreduction and storage upright at 4° C. for 42 days. After 42 days, the intermediate RCC product units were removed from storage, well-mixed and transferred into 50 mL conical tubes. Samples of the RCC were then aliquoted into 5 mL polypropylene tubes either undiluted (control) or diluted at a 1:1 volume ratio. For those RCC samples that were diluted, they were diluted with one of the following solutions of known-osmolarity: Adsol, phosphate buffer saline (PBS), standard saline solutions (0.7%, 0.9% 1.1%, 1.3%/c; and 1.5%), citrate phosphate dextrose anticoagulant (CPD), and anticoagulant citrate dextrose formula A (ACD-A). Samples were thoroughly mixed and held at room temperature for 0, 1, or 4 hours. Supernatants from the samples were prepared for K+, free hemoglobin, lactate, and total protein analysis by double centrifugation at 2600×g for 10 minutes and normalized to hematocrit.

Figure 3A:
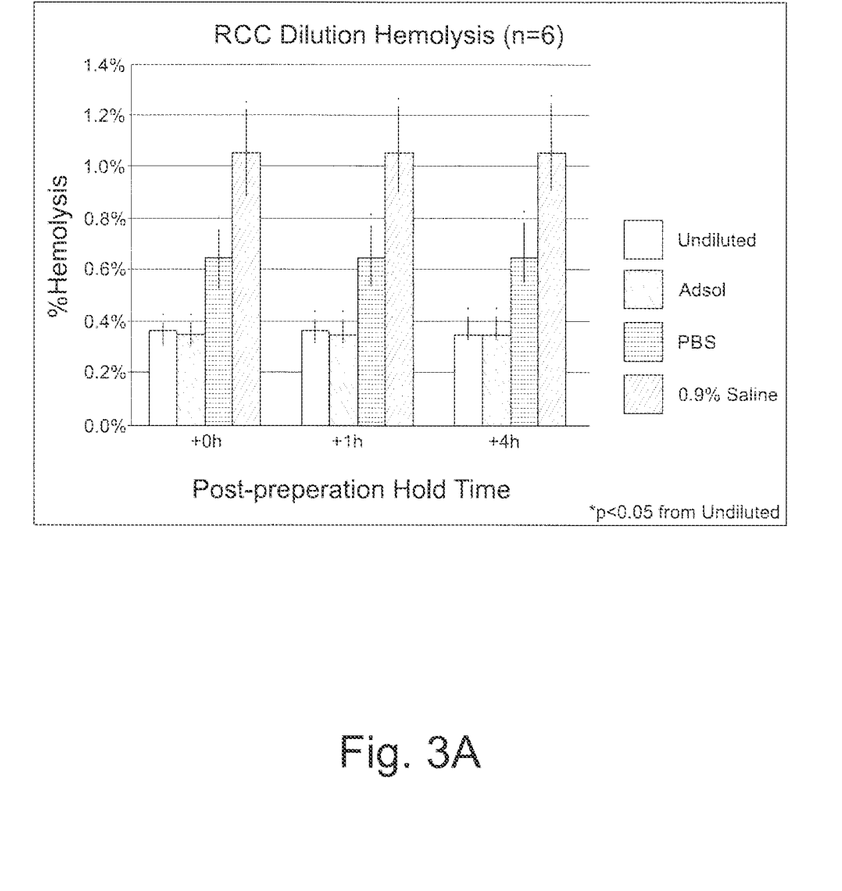
FIG. 3A is a chart of observed hemolysis levels within a study conducted to evaluate washing fluid properties, according to an exemplary embodiment.
Figure 3B:
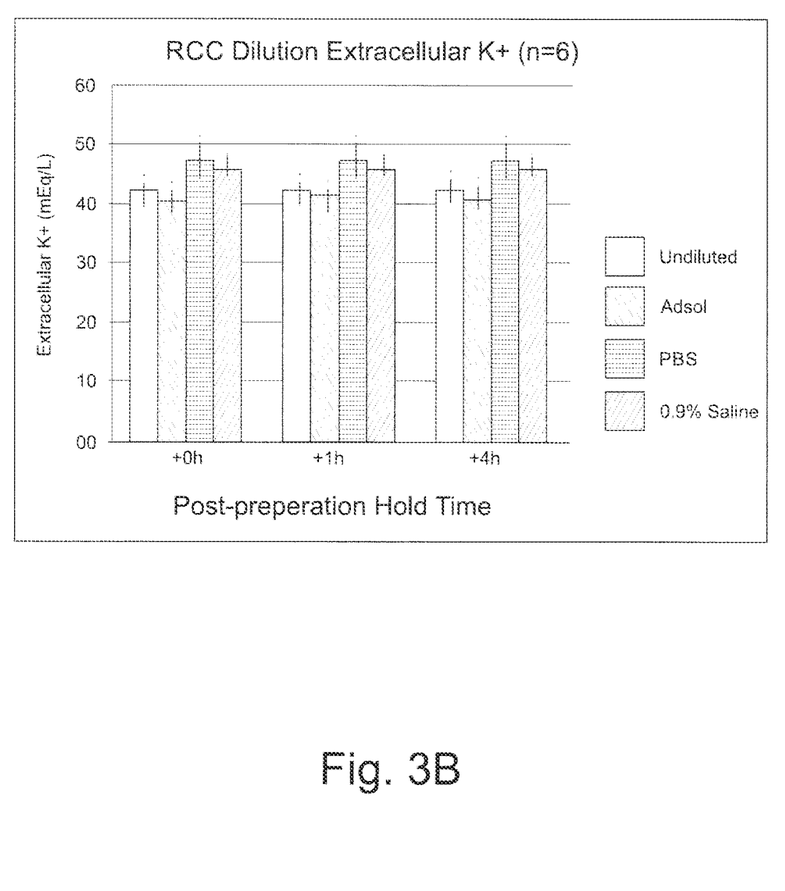
FIG. 3B is a chart of observed extracellular potassium levels within a study conducted to evaluate washing fluid properties, according to an exemplary embodiment.

Turning to FIGS. 3A and 3B, observed hemolysis and extracellular potassium levels were charted for different hold times and dilution solutions. The RCC Dilution Hemolysis chart in FIG. 3A shows that free hemoglobin levels increased above the undiluted control for samples diluted 1:1 in both 0.9% saline and PBS solutions, while free hemoglobin levels remained on par with the undiluted control for samples diluted with Adsol. The RCC Dilution Extracellular K+ chart in FIG. 3B shows that extracellular potassium levels did not significantly increase above controls for any samples measured. Although not charted, total protein levels and total lactate levels also did not increase above controls for the samples measured. Holding for 0, 1, or 4 hours did not exhibit significant differences in hemolysis or extracellular component levels. The results of FIGS. 3A and 3B indicate that intermediate RCCs washed with normal saline or PBS solution may induce hemolysis with a correspondingly increased level of free hemoglobin, without corresponding increases in extracellular K+, protein, or lactate.

Figure 4A:
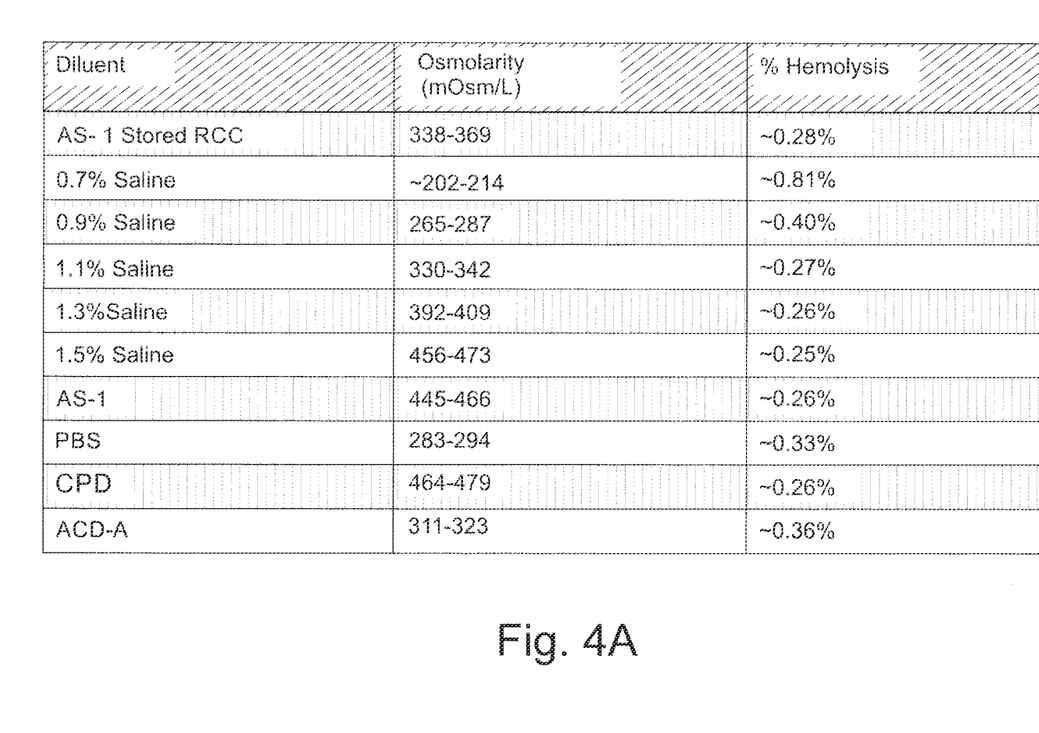
FIG. 4A is a chart listing different osmolarities of different wash solutions and resulting hemolysis of red cells, according to an exemplary embodiment.
Figure 4B:
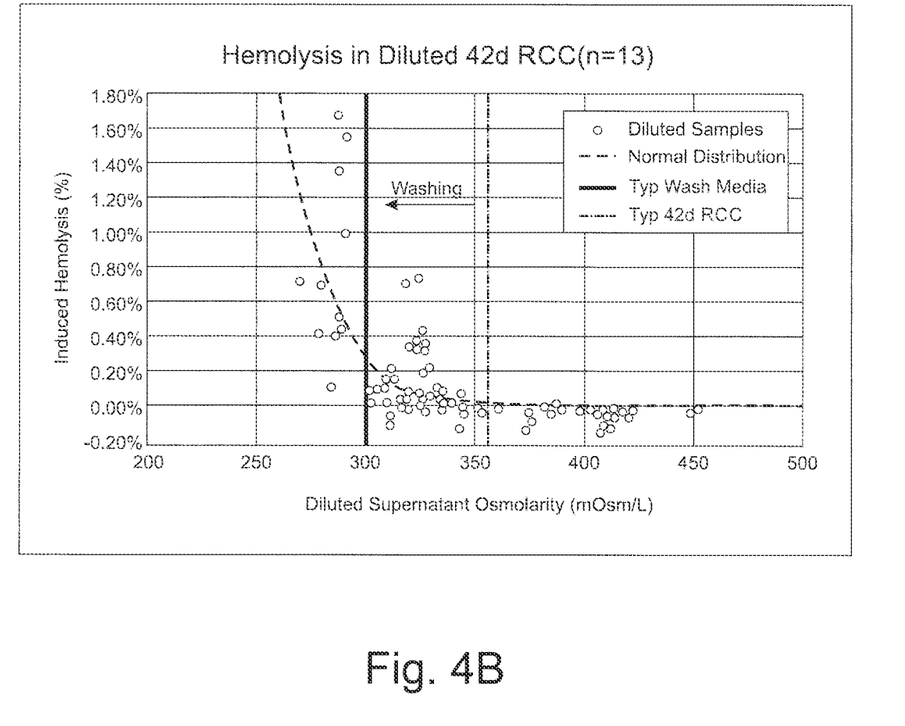
FIG. 4B is a graph showing observed hemolysis of RCCs from dilution with solutions of varied osmolarities, according to an exemplary embodiment.

Turning to FIG. 4A, a chart listing the different osmolarities of the different wash solutions is shown. FIG. 4A also lists the percent hemolysis of the red blood cells that results subsequent to washing the intermediate RCC samples with each wash solution. Observed hemolysis of RCCs from dilution with the solutions of varied osmolarities subsequent to 42 days of RCC storage is also shown in FIG. 4B. FIG. 4B shows that the osmolarity of unwashed RCCs that have been stored for 42 days is approximately 360 mOsmiL and that the osmolarity of a typical wash solution such as PBS or 0.9% saline is approximately 300 mOsmiL. The normal curve demonstrates that as the diluted supernatant osmolarity decreases farther away from that of the intermediate RCCs stored for 42 days, hemolysis of the cells increases to yield higher free hemoglobin levels. It can also be seen from the normal curve and FIG. 4B that RCCs diluted with wash media of higher osmolarity than that of the stored intermediate RCC sample do not exhibit increases in free hemoglobin. RCCs washed with solutions similar or higher in osmolarity to the intermediate RCC sample may result in washed products with reduced free hemoglobin levels, according to an exemplary embodiment. These results are also consistent with FIG. 4A, in which plasma hemoglobin levels drop significantly between 0.9% saline to 1.1% saline, which has an osmolarity similar to that of the intermediate RCCs stored for 42 days in Adsol.

Figure 5:
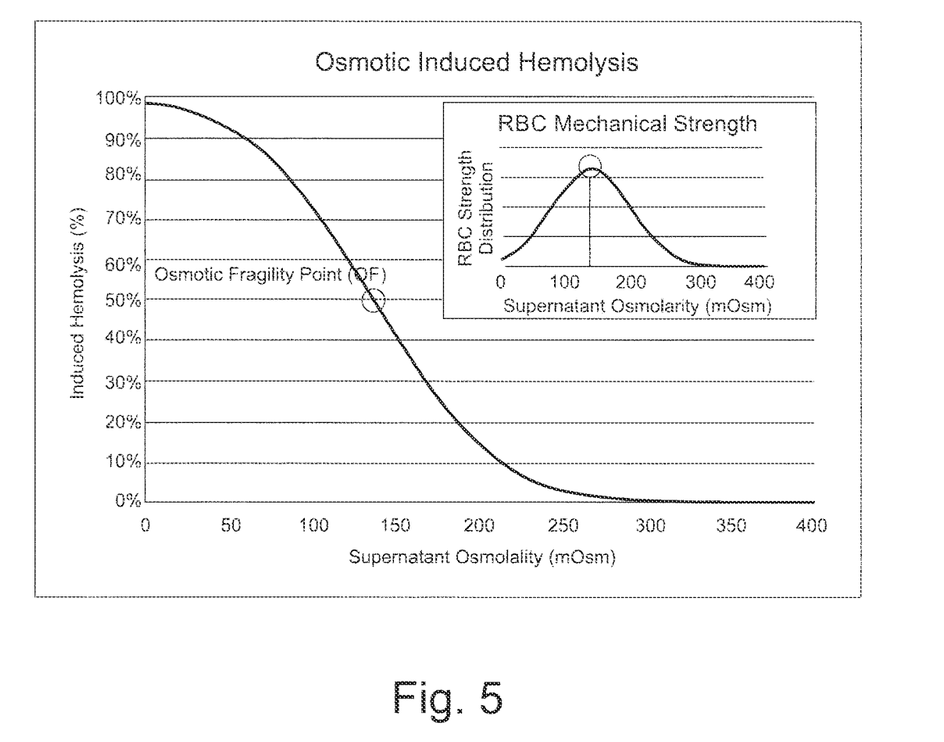
FIG. 5 is a graph of percentage of induced hemolysis versus supernatant osmolarity, according to an exemplary embodiment.

Turning to FIG. 5, percentage of induced hemolysis versus supernatant osmolarity is shown. It can be seen in FIG. 5 that nearly 100% of cells lyse when supernatant osmolarity is zero and cell lysis plateaus when supernatant osmolarity is approximately 300 mOsm. The osmotic fragility point, defined as the point at which exactly half the cells have lysed is shown in FIG. 5 to be approximately 140 mOsm. A related graph of RBC mechanical strength distribution is shown in the graphical insert of FIG. 5. The RBC strength distribution graph shows the point of osmotic rupture for a population of RBCs. At 0 mOsm, almost no cells are shown to withstand lysis. Most cells, as indicated by the middle of the curve, are shown to lyse at approximately 140 mOsm. At 300 mOsm, only the weakest cells are shown to lyse.

Subsequent to washing the intermediate RCCs with a suitable wash media as described above, the wash media may be separated from the RCCs according to known procedures. The resulting isolated RCCs may be transfused to a recipient and may be described as readily transfusible.

Figure 6:
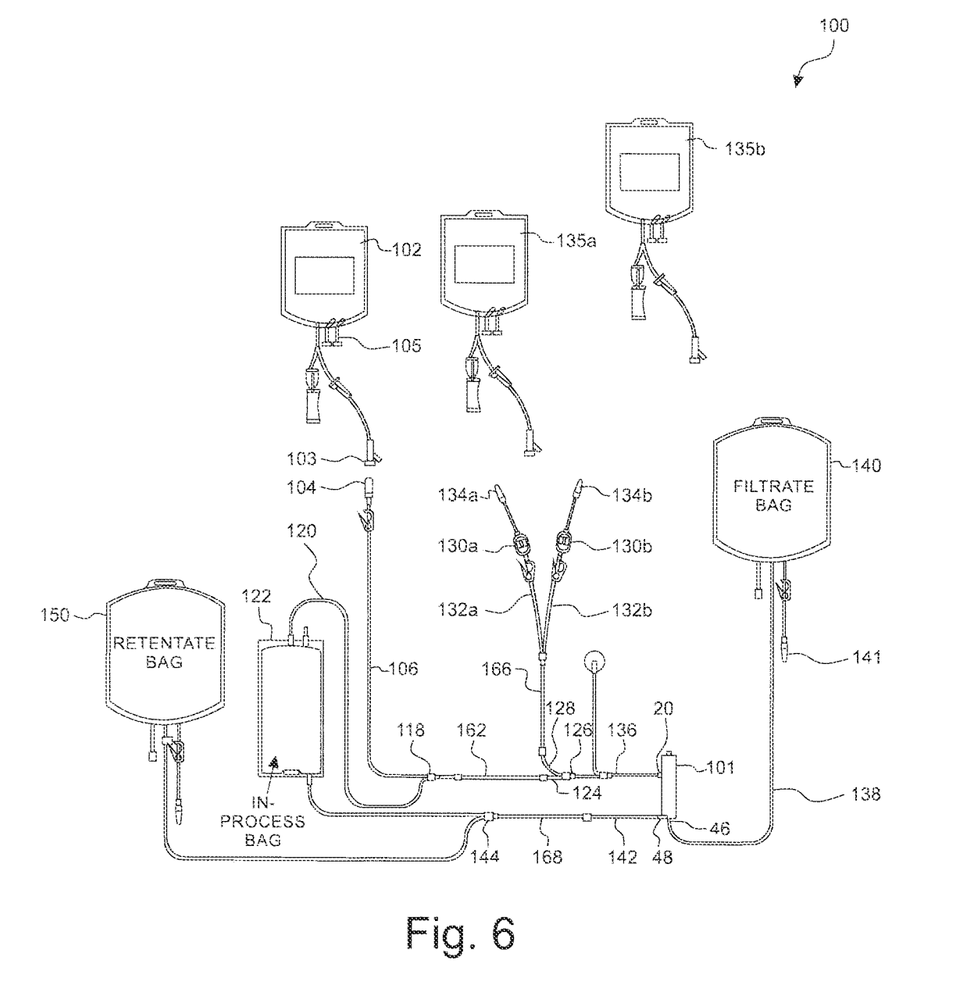
FIG. 6 is a processing set which may be employed to provide a red blood cell product according to the disclosure herein, according to an exemplary embodiment.

A variety of systems may be used to obtain a red blood cell product in accordance with the present disclosure. For example, FIG. 6 shows an embodiment of a system (processing set) 100 which may be employed to provide a red blood cell product according to the disclosure herein. In this embodiment, this system includes a plurality of interconnected containers in open or openable fluid communication with each other. A source container 102 contains the blood to be processed and may initially not be connected to the remainder of the processing set 100. The containers and tubing defining the various flow paths may be made from a suitable plastic material of the type used in the medical field, such as, but not limited to polyvinyl chloride, acrylics, or polyolefin. The materials used for the containers and tubing and, thus, the entire set are/is sterilizable by, but not limited to, autoclaving.

As shown in FIG. 6, processing set 100 may include a plurality of plastic containers interconnected by tubing segments. Set 100 may include a first container 102 for holding the source of blood such as, but not limited to, whole blood to be processed in accordance with the method described herein. Source container 102 may have one or more access sites 103, 105, one of which may be adapted for (sterile) connection to fluid circuit 100 at docking site 104. Preferably, source containers may be attached in a sterile manner by employing sterile docking devices, such as the BioWelder or the SCD !IB Tubing Welder, available in the market. A second access port 105 may also be provided for extracting fluid from the source container 102.

Set 100 also may include satellite containers 122, 140, and 150. Container 150, initially empty, may receive the final red blood cell product. Access sites 134a, 134b may be provided to establish flow communication with containers 135a, 135b containing an additive solution and/or wash media as described above, while container 140, also initially empty, may receive plasma separated from source blood in container 102. The container 102 may be in fluid communication with each of the other bags through flow paths defined by tubing. Flow through processing set 100 may be controlled by flow controllers such as clamps, frangible connectors, valves, or switches.

According to one embodiment for providing a red blood cell product, an automated separation and wash procedure is described. Blood such as, but not limited to whole blood or concentrated red cells, may be received by container 102. As noted above, if the blood in container 102 is whole blood, the volume may typically be between 400-500 m L. The blood may be subjected to a separation step through a spinning membrane separator 101 in FIG. 6 to separate the blood into red blood cell concentrate and plasma. To this end, blood from container 102 may be continuously pumped toward spinning membrane separator 101. Prior to entering the separator 101, the blood may be continuously mixed at connector 126 with a volume of wash solution from container 135a or container 135b. After separation, plasma, supernatant, and wash media may then be filtered to a second container 140. The red blood cell concentrate may be directed out of port 48 into intermediate container 122 and may include about 200 mL of red cells and about 10-30 mL of plasma and anticoagulant (e.g., CPD). The blood may be processed until container 102 is empty. A rinse of the processing set 100 may optionally be performed to ensure all cells in the set 100 are directed to the intermediate container 122.

After the plasma has been expressed from the container and physically separated from red blood cell concentrate (by, for example, an Optipress or other component extractor), a selected volume, approximately 200 mL, of an additive solution of the type described above may be transferred from container 135a or 135b to the intermediate container 122 containing the red blood cell concentrate to form an intermediate red blood cell product. The intermediate red blood cell product may then be placed in storage or be further processed for immediate use.

Subsequent to the formation of the intermediate red blood cell product (or subsequent to its storage), the intermediate red blood cell product may be further processed by spinning membrane separation. The intermediate red blood cell product in intermediate container 122 may again be pumped toward the separator 101. Prior to entering the separator, the intermediate red blood cell product may be continuously mixed at connector 126 with a volume of wash solution from container 135a or container 135b. After separation, plasma, supernatant, and wash media may then be filtered to a second container 140. The resulting red blood cell concentrate may be directed out of port 48 into a final product container 150. Preferably, the intermediate red blood cell product is subjected to separation such that the resulting red blood cell concentrate has a hematocrit of approximately 80%. As a consequence of further separating the supernatant and residual plasma from the intermediate red blood cell product, the plasma content of the red blood cell composition may be further reduced. A rinse of the processing set 100 may optionally be performed to ensure all cells in the set 100 are directed to the final product container 150.

Subsequently, a selected volume of a wash media of the type described above may be transferred again from container 135a or 135b to the final product container 150 containing the resulting red blood cell concentrate. The resulting red blood cell concentrate suspended in wash media may be further processed by, for example, separating the supernatant (containing residual plasma, residual additive solution, and the wash media) from the red blood cell concentrate. The final isolated RCCs, transferred to container 150, may be transfused to a recipient and may be described as readily transfusible.

Without limiting the foregoing description, in accordance with one aspect of the subject matter herein, there is provided a system for washing red blood cells. A separator is configured to separate a quantity of blood into concentrated red blood cells having a hematocrit of at least 60% and a volume of 150-250 mL, and a supernatant component. A flow controller is in communication with the separator. The flow controller is configured to remove the supernatant component to provide an initial red blood cell concentrate. The flow controller is also configured to combine 50-500 mL of an additive solution with the red blood cell concentrate to provide an intermediate red blood cell product that is intended for storage for a period of time of 42 days or less, wherein the intermediate red blood cell product at the end of storage has an osmolarity value between 202-479 mOsm/L. The intermediate red blood cell product comprising the osmolarity value between 202-479 mOsm/L is washed with a washing solution having an osmolarity value higher than that of the intermediate red blood cell product comprising the osmolarity value between 202-479 mOsm/L.

In accordance with a second aspect which may be used or combined with the immediately preceding aspect, the additive solution comprises glucose, mannitol, and adenine.

In accordance with a third aspect which may be used or combined with any of the preceding aspects, the osmolarity value of the intermediate red blood cell product at the end of storage is 338-369 mOsm/L.

In accordance with a fourth aspect which may be used or combined with any of the first and second aspects, the osmolarity value of the intermediate red blood cell product at the end of storage is 202-294 mOsm/L.

In accordance with a fifth aspect which may be used or combined with the first aspect, the osmolarity value of the intermediate red blood cell product at the end of storage is 392-479 mOsm/L.

In accordance with a sixth aspect, there is provided a system for washing red blood cells, comprising a separator configured to separate a quantity of blood into concentrated red blood cells and a supernatant component. A flow controller is in communication with the separator. The flow controller is configured to remove said supernatant component to provide an initial red blood cell concentrate. An additive solution is combined with said red blood cell concentrate to provide an intermediate red blood cell product that is intended for storage for a period of time. The intermediate red blood cell product that has been stored for a period of time is washed with a washing solution having an osmolarity value higher than that of the intermediate red blood cell product.

In accordance with a seventh aspect which may be used or combined with the sixth aspect, the quantity of blood is approximately 400-500 mL in volume, the intermediate red blood cell product has a hematocrit of at least 60%, and the volume of additive solution added to the red blood cell concentrate is between 50 and 500 mL.

In accordance with an eighth aspect which may be used or combined with any of the sixth and seventh aspects, the period of time for storing the intermediate red blood cell product is not greater than 42 days.

In accordance with a ninth aspect which may be used or combined with any of the sixth through eighth aspects, the step of separating the quantity of blood into concentrated red blood cells and a supernatant component is performed by at least one of a centrifuge and spinning membrane.

In accordance with a tenth aspect which may be used or combined with any of the sixth through ninth aspects, extracellular component levels within the washed intermediate red blood cell product is substantially similar to the levels within the unwashed intermediate red blood cell product.

In accordance with an eleventh aspect which may be used or combined with any of the sixth through tenth aspects, the osmolarity value of the intermediate red blood cell product is 338-369 mOsm/L.

In accordance with a twelfth aspect which may be used or combined with any of the sixth through tenth aspects, the osmolarity value of the intermediate red blood cell product is 202-294 mOsm/L.

In accordance with a thirteenth aspect which may be used or combined with any of the sixth through twelfth aspects, the additive solution comprises glucose, mannitol, and adenine.

In accordance with a fourteenth aspect, there is provided a system for processing blood cells comprising a flow controller configured to add a selected volume of additive solution to a quantity of blood. A separator is in communication with the flow controller configured to separate the quantity of blood into concentrated red blood cells and a supernatant component The supernatant component comprises at least plasma and additive solution, and the concentrated red blood cell component comprises red blood cells and a volume of remaining supernatant The flow controller is configured to wash the concentrated red blood cell component with a wash media comprising an osmolarity value higher than the osmolarity value of the concentrated red blood cell component, and remove substantially all of the wash media and remaining supernatant to provide a treated red blood cell concentrate. A percentage of red cells that have undergone hemolysis during washing and removal of wash media is less than 0.3% of the red cells from the concentrated red blood cell component.

In accordance with a fifteenth aspect which may be used or combined with the immediately preceding aspect, the quantity of blood is approximately 400-500 mL in volume, the intermediate red blood cell product has a hematocrit of at least 60%, and the volume of additive solution added to the red blood cell concentrate is between 50 and 500 mL.

In accordance with a sixteenth aspect which may be used or combined with any of the fourteenth and fifteenth aspects, the separation of the quantity of blood into concentrated red blood cells and a supernatant component is performed by at least one of a centrifuge and spinning membrane.

In accordance with a seventeenth aspect which may be used or combined with any of the fourteenth through sixteenth aspects, extracellular component levels within the treated red blood cell concentrate is substantially similar to the levels within the quantity of blood.

In accordance with an eighteenth aspect which may be used or combined with any of the fourteenth through seventeenth aspects, the osmolarity value of the concentrated red blood cell component is 338-369 mOsm/L.

In accordance with a nineteenth aspect which may be used or combined with any of the fourteenth through seventeenth aspects, the osmolarity value of the intermediate red blood cell product is 202-294 mOsm/L.

In accordance with a twentieth aspect which may be used or combined with any of the fourteenth through nineteenth aspects, the additive solution comprises glucose, mannitol, and adenine.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A system for washing red blood cells, comprising:
a separator configured to separate a quantity of blood into concentrated red blood cells and a supernatant component;
a flow controller in communication with the separator, wherein the flow controller is configured to:
remove said supernatant component to provide an initial red blood cell concentrate;
combine an additive solution with said red blood cell concentrate to provide an intermediate red blood cell product that is intended for storage for a period of time; and
wash the intermediate red blood cell product that has been stored for a period of time with a washing solution.

2. The system of claim 1, wherein the quantity of blood is approximately 400-500 mL in volume, the intermediate red blood cell product has a hematocrit of at least 60%, and the volume of additive solution added to the red blood cell concentrate is between 50 and 500 mL.

3. The system of claim 1, wherein the period of time for storing the intermediate red blood cell product is not greater than 42 days.

4. The system of claim 1, wherein the step of separating the quantity of blood into concentrated red blood cells and a supernatant component is performed by at least one of a centrifuge and spinning membrane.

5. The system of claim 1, wherein extracellular component levels within the washed intermediate red blood cell product is substantially similar to the levels within the unwashed intermediate red blood cell product.

6. The system of claim 1, wherein the additive solution comprises glucose, mannitol, and adenine.

7. A system for processing blood cells comprising:
a flow controller configured to add a selected volume of additive solution to a quantity of blood;
a separator in communication with the flow controller configured to separate the quantity of blood into concentrated red blood cells and a supernatant component, wherein the supernatant component comprises at least plasma and additive solution, and wherein the concentrated red blood cell component comprises red blood cells and a volume of remaining supernatant;
wherein the flow controller is configured to wash the concentrated red blood cell component with a wash media, and remove substantially all of the wash media and remaining supernatant to provide a treated red blood cell concentrate;
wherein a percentage of red cells that have undergone hemolysis during washing and removal of wash media is less than 0.3% of the red cells from the concentrated red blood cell component.

8. The system of claim 7, wherein the quantity of blood is approximately 400-500 mL in volume, the intermediate red blood cell product has a hematocrit of at least 60%, and the volume of additive solution added to the red blood cell concentrate is between 50 and 500 mL.

9. The system of claim 7, wherein the separation of the quantity of blood into concentrated red blood cells and a supernatant component is performed by at least one of a centrifuge and spinning membrane.

10. The system of claim 7, wherein extracellular component levels within the treated red blood cell concentrate is substantially similar to the levels within the quantity of blood.

11. The system of claim 7, wherein the additive solution comprises glucose, mannitol, and adenine.

12. A method for processing blood cells comprising:
adding a selected volume of additive solution to a quantity of blood;
separating the quantity of blood into concentrated red blood cells and a supernatant component, wherein the supernatant component comprises at least plasma and additive solution, and wherein the concentrated red blood cell component comprises red blood cells and a volume of remaining supernatant;
washing the concentrated red blood cell component with a wash media;
removing substantially all of the wash media and remaining supernatant to provide a treated red blood cell concentrate;
wherein the percentage of red cells that have undergone hemolysis during washing and removal of wash media is less than 0.3% of the red cells from the concentrated red blood cell component.

13. The method of claim 12, wherein the quantity of blood is approximately 400-500 mL in volume, the intermediate red blood cell product has a hematocrit of at least 60%, and the volume of additive solution added to the red blood cell concentrate is between 50 and 500 mL.

14. The method of claim 12, wherein the separation of the quantity of blood into concentrated red blood cells and a supernatant component is performed by at least one of a centrifuge and spinning membrane.

15. The method of claim 12 wherein extracellular component levels within the treated red blood cell concentrate is substantially similar to the levels within the quantity of blood.

16. The method of claim 12, wherein the additive solution comprises glucose, mannitol, and adenine.

17. A method for washing red blood cells in the system of claim 1 comprising establishing flow communication between a source of said quantity of blood and said separator.

18. The method of claim 17 comprising collecting said intermediate red blood cell product in an intermediate product container of said processing set.

19. The method of claim 18 comprising rinsing said processing set after said collecting of said intermediate red blood cell product.

20. The method of claim 19 comprising removing said supernatant by compressing said intermediate container in a blood component extractor.

* * * * *